(12) United States Patent
Kawasaki

(10) Patent No.: US 7,410,953 B2
(45) Date of Patent: Aug. 12, 2008

(54) ANTICANCER AGENT

(75) Inventor: Toshisuke Kawasaki, Hirakata (JP)

(73) Assignee: Takara Bio, Inc., Shiga-Ken (JP)

( * ) Notice: Subject to any disclaimer, the term of this patent is extended or adjusted under 35 U.S.C. 154(b) by 745 days.

(21) Appl. No.: 09/971,475

(22) Filed: Oct. 4, 2001

(65) Prior Publication Data

US 2002/0086817 A1    Jul. 4, 2002

Related U.S. Application Data

(60) Division of application No. 09/468,705, filed on Dec. 21, 1999, which is a continuation of application No. PCT/JP98/03697, filed on Aug. 19, 1998.

(30) Foreign Application Priority Data

Aug. 21, 1997    (JP)    ............................. 1997/239113

(51) Int. Cl.
*A61K 31/70* (2006.01)
*A01N 63/00* (2006.01)
*A61K 38/00* (2006.01)

(52) U.S. Cl. ........................................ 514/44; 424/93.8

(58) Field of Classification Search .................... 514/44
See application file for complete search history.

(56) References Cited

U.S. PATENT DOCUMENTS

| 5,091,178 A | 2/1992 | Hellstrom et al. |
|---|---|---|
| 5,270,199 A | 12/1993 | Ezekowitz |
| 5,951,976 A * | 9/1999 | Segal .................... 424/93.21 |

FOREIGN PATENT DOCUMENTS

| WO | WO 89/01519 | 2/1989 |
|---|---|---|
| WO | WO 92/07579 | 5/1992 |
| WO | WO 94/16716 | 8/1994 |
| WO | WO 99/64453 | 12/1999 |

OTHER PUBLICATIONS

Verma et al (Nature, 1997, vol. 389, pp. 239-242).*
Eck et al (Gene-Based Therapy, In: the Pharmacological Basis of Therapeutics, Goodman and Gilman, Ed.s, 1996, pp. 77-101).*
Orkin et al (A Report and Recommedation of the Panel to Assess the NIH Investment in Research on Gene Therapy @, NIH, 1995).*
Schulze et al (Trends in Immunology, 2004, vol. 25, pp. 689-664).*
Bodey et al, (Anticancer Research, 2000, vol. 20, pp. 2664-2676).*
Vile et al (Gene Therapy, 2000, vol. 7, pp. 2-8).*
Addisson et al (PNAS, 1995, vol. 92, pp. 8522-8526).*
International Search Report for International Appl. PCT/JP98/039697, Oct. 19, 1998.
International Preliminary Examination Report for PCT/JP98/03697, Aug. 27, 1999.
Fujita T et al., "Mannose-binding Protein Recognizes Glioma Cells: In vitro Anaylsis of Complement Activation on Glioma Cells via the Lectin Pathway," *Jpn. J. Cancer Res.*, 86:187-192 (Feb. 1995).
Sastry K et al., "The Human Mannose-Binding Protein Gene," *J. Exp. Med.*, 170:1175-1189 (Oct. 1989).
Kunio, Cationic Liposomes, "Gene Therapy,"*Protein, Nucleic Acid, and Enzyme*, Special Extra Issue 40(17):2577-2582 (1995). (Japanese language and English translation of Fig. 1).

Makamura K et al., *Molecular Biology of Cells,* (2nd ed.), pp. 1031-1036 (1990). (Japanese language with English summary).
Frisch, Christian et al., A Soluble immunoglobin Variable Domain Withoout a Disulfide Bridge: Construction, Accumulation in the Cytoplasm of *E. coli*, Purification and Physicochemical Characterization, *Biol. Chem. Hopp-Seyler*, 375:353-356 (May 1994).
Mathews, Christopher K. et al., *Biochemistry,* 2nd ed., (Menlo Park, CA:The Benjamin/Cummings Publishing Co., Inc., 1996), pp. 165-171.
Kim, Hyun-Won et al., "Restoring Allosterism With Compensatory Mutations in Hemoglobin," *Proc. Natl. Acad. Sci. USA*, 91:11547-11551 (Nov. 1994).
Kurata, Hiroshi et al., "Structure and Function of Mannan-Binding Proteins Isolated from Human Liver and Serum," *J. Biochem.* 115:1148-1154 (1994).
Ma, Yong et al., "Functional Expression of Human Mannan-Binding Proteins (MBPs) in Human Hepatoma Cell Lines Infected by Recombinant Vaccinia Virus: Post-Translational Modification, Molecular Assemby, and Differentiation of Serum and Liver MBP," *J. Biochem.* 122:810-818 (1997).
Kozutsumi, Yasunori et al. "Isolation and Characterization of a Mannan-Building Protein From Rabbit Serum," *Biochemical and Biophysical Research Communications,* 95:658-664 (Jul. 31, 1980).
Neurath, Hans, ed., *Perspectives in Biochemistry,* vol. 1 (Washington:American Chemical Society, 1989), pp. 6-9.
Garred P., et al., "Increased Frequency of Homozygosity of Abnormal Mannan-Binding-Protein Alleles in Patients with Suspects Immunodeficiency," *The Lancet,* vol. 346, pp. 941-943 (Oct. 7, 1995).
Ohta M., et al., "Complement-Dependent Cytotoxic Activity of Serum Mannan-Binding Protein Towards Mammalian Cells with Surface-Exposed High-Mannose Type Glycans," *Medline, Glycoconjugate Journal,* vol. 11, pp. 304-308 (Aug. 1994).
Wawotzny, R., et al., "Are Matrix-Immobilized Neoglyocproteins, Plant and Human Lectins and Carbohydrate-Binding Anitbodies from Human Serum Mediators of Adhesion in Vitro for Carcinoma and Lymphosarcoma Cells?" *Biosis, Anticancer Research,* vol. 15, pp. 169-174 (1995).
Sabine, A., "Evidence for the Involvement of Serum Lectins and Carbohydrate-Binding Antibodies in Tumor Defence," *Anticancer Research,* vol. 15, p. 1816 (1995).
Ma Yong, et al., "Antitumor activity of Mannan-Binding Protein In Vivo as Revealed by a Virus Expression System: Mannan-Binding Protein-Dependent Cell-Mediated Cytotoxicity," *Proceeding of the National Academy of Sciences of the United States of America,* vol. 96, pp. 371-375 (Jan. 1999).

* cited by examiner

Primary Examiner—Karen A Canella
(74) *Attorney, Agent, or Firm*—Kolisch Hartwell, P.C.

(57) ABSTRACT

The present invention is to offer a pharmaceutical agent which is capable of suppressing the growth of cancer in cancer cells and the surrounding tissues thereof or in tissue of non-diseased part. An anticancer agent having a mannan-binding protein or gene thereof as an effective component. Examples of a mannan-binding protein are a protein which has an amino acid sequence described in SEQ ID NO:1 of the Sequence Listing and a protein which has an amino acid sequence where one or more amino acid residue(s) is/are subjected to at least one of substitution, deletion, addition and insertion in the amino acid sequence and also has an activity as mannan-binding protein. Examples of a gene are a gene which codes an amino acid sequence described in SEQ ID NO:1 or NO:2 of the Sequence Listing or modified amino acid sequence, or a gene which contains said gene.

3 Claims, 3 Drawing Sheets

SEQUENCE LISTING

```
<160> NUMBER OF SEQ ID NOS: 2

<210> SEQ ID NO 1
<211> LENGTH: 228
<212> TYPE: PRT
<213> ORGANISM: Homo sapiens

<400> SEQUENCE: 1

Glu Thr Val Thr Cys Glu Asp Ala Gln Lys Thr Cys Pro Ala Val Ile
 1               5                  10                  15

Ala Cys Ser Ser Pro Gly Ile Asn Gly Phe Pro Gly Lys Asp Gly Arg
                20                  25                  30

Asp Gly Thr Lys Gly Glu Lys Gly Glu Pro Gly Gln Gly Leu Arg Gly
            35                  40                  45

Leu Gln Gly Pro Pro Gly Lys Leu Gly Pro Pro Gly Asn Pro Gly Pro
        50                  55                  60

Ser Gly Ser Pro Gly Pro Lys Gly Gln Lys Gly Asp Pro Gly Lys Ser
 65                 70                  75                  80

Pro Asp Gly Asp Ser Ser Leu Ala Ala Ser Glu Arg Lys Ala Leu Gln
                85                  90                  95

Thr Glu Met Ala Arg Ile Lys Lys Trp Leu Thr Phe Ser Leu Gly Lys
            100                 105                 110

Gln Val Gly Asn Lys Phe Phe Leu Thr Asn Gly Glu Ile Met Thr Phe
        115                 120                 125

Glu Lys Val Lys Ala Leu Cys Val Lys Phe Gln Ala Ser Val Ala Thr
        130                 135                 140

Pro Arg Asn Ala Ala Glu Asn Gly Ala Ile Gln Asn Leu Ile Lys Glu
145                 150                 155                 160

Glu Ala Phe Leu Gly Ile Thr Asp Glu Lys Thr Glu Gly Gln Phe Val
                165                 170                 175

Asp Leu Thr Gly Asn Arg Leu Thr Tyr Thr Asn Trp Asn Glu Gly Glu
            180                 185                 190
```

```
Pro Asn Asn Ala Gly Ser Asp Glu Asp Cys Val Leu Leu Leu Lys Asn
        195                 200                 205
Gly Gln Trp Asn Asp Val Pro Cys Ser Thr Ser His Leu Ala Val Cys
    210                 215                 220
Glu Phe Pro Ile
225

<210> SEQ ID NO 2
<211> LENGTH: 684
<212> TYPE: DNA
<213> ORGANISM: Homo sapiens

<400> SEQUENCE: 2
gaaactgtga cctgtgagga tgcccaaaag acctgccctg cagtgattgc ctgtagctct      60
ccaggcatca acggcttccc aggcaaagat gggcgtgatg gcaccaaggg agaaaagggg     120
gaaccaggcc aagggctcag aggcttacag ggccccctg gaaagttggg gcctccagga      180 aatccaggc cttctgggtc accaggacca aagggccaaa aaggagaccc tggaaaaagt      240
ccggatggtg atagtagcct ggctgcctca gaaagaaaag ctctgcaaac agaaatggca     300
cgtatcaaaa agtggctgac cttctctctg ggcaaacaag ttgggaacaa gttcttcctg     360
accaatggtg aaataatgac ctttgaaaaa gtgaaggcct tgtgtgtcaa gttccaggcc     420
tctgtggcca cccccaggaa tgctgcagag aatggagcca ttcagaatct catcaaggag     480
gaagccttcc tgggcatcac tgatgagaag acagaagggc agtttgtgga tctgacagga     540
aatagactga cctacacaaa ctggaacgag ggtgaaccca acaatgctgg ttctgatgaa     600
gattgtgtat tgctactgaa aaatggccag tggaatgacg tcccctgctc cacctcccat     660
ctggccgtct gtgagttccc tatc                                           684
```

ANTICANCER AGENT

This application is a divisional of U.S. patent application Ser. No. 09/468,705 for an ANTICANCER AGENT, filed on Dec. 21, 1999, the disclosure of which is hereby incorporated by reference, which is a continuation of PCT Application No. PCT/JP98/03697, filed on Aug. 19, 1998.

TECHNICAL FIELD

The present invention relates to a pharmaceutical agent useful in the pharmaceutical field in which specific protein concentrations in cancer cells and the surrounding tissues thereof or in tissues of non-diseased part are enhanced whereby growth of the cancer is suppressed.

PRIOR ART

In recent years, there have been significant progresses in therapeutic method for cancer such as chemotherapy for cancer although cancer is still a disease which occupies an important position as a cause for death throughout the world. Consequently, there has been a strong demand for the development of a new and really effective therapeutic method for cancer.

Besides immunoglobulin such as blood group-recognizing antibody, there is a group of functional proteins which are generally called "animal lectin" in animal tissues and body fluids as a protein which recognizes sugar.

During the course of studies on the animal lectin, the present inventors found type C lectin which binds to mannose (Man) or N-acetylglucosamine (GlcNAc) in a calcium-dependent manner from mammalian liver and serum and named "mannan-binding protein" (MBP) [*Biochemical and Biophysical Research Communications*, 81(1), 1018-1024 (1978); *Biochemical and Biophysical Research Communications*, 95(2), 658-664 (1980); and others].

It has been further succeeded in obtaining the MBP from human liver and serum and also genes thereof [*Journal of Biochemistry*, 115(6), 1148-1154 (1994)]. Incidentally, the mannan-binding protein is sometimes called "mannose-binding protein" or "mannan-binding lectin".

During the course of studies concerning structure and function of the MBP, the present inventors have clarified that the serum MBP activates a complement system by means of a classical route or a lectin route without depending upon antibody or C1q which is a complement component. It has been also known that the serum MBP exhibits a direct biophylaxis action. For example, it has been known that infection is suppressed as a result of binding of MBP with oligomannose type sugar chains on envelope glycoprotein of human immunodeficiency virus or MBP promotes the removal of yeasts or a certain type of gram-negative bacteria by phagocytes.

However, it has not been known at all up to now for the action of MBP to cancer cells or cancer tissues.

PROBLEMS TO BE SOLVED BY THE INVENTION

An object of the present invention is to offer a pharmaceutical agent which is capable of suppressing the growth of cancer in cancer cells and the surrounding tissues thereof or in tissue of non-diseased part.

MEANS TO SOLVE THE PROBLEMS

In order to achieve the above objects, the present inventors have carried out various investigations and, quite unexpectedly, they have found that, between the tumor bearing animals to which the gene coding for MBP is administered and those to which the gene coding for MBP is not administered, the growing ability of cancer cells in the tumor bearing animals administered with the gene coding for MBP is clearly suppressed whereupon the present invention has been accomplished.

To sum up, the present invention relates to an anticancer agent which is characterized in having a mannan-binding protein or gene thereof as an effective component.

BEST MODE FOR CARRYING OUT THE INVENTION

Figure 1:
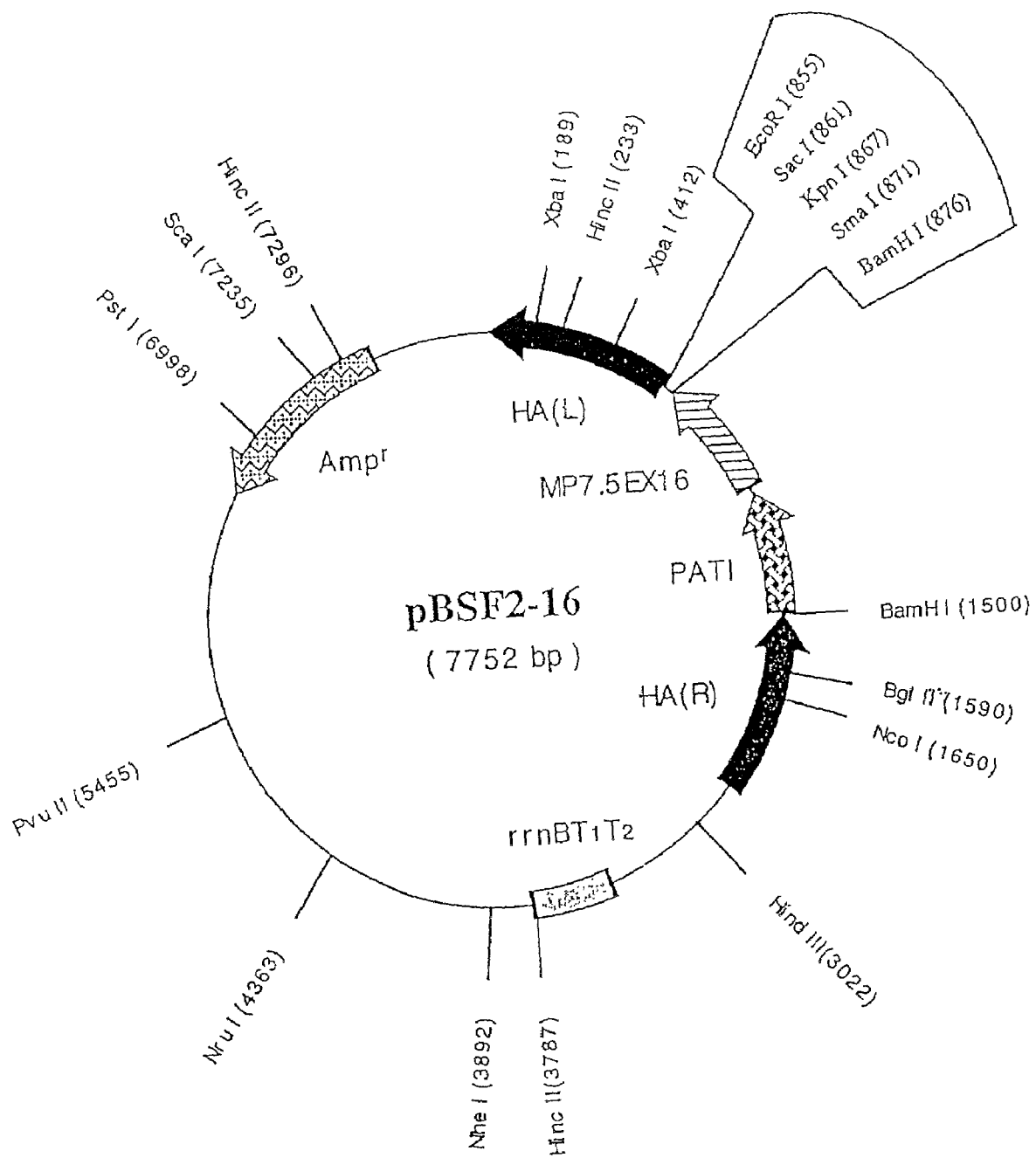
FIG. 1 is a drawing which shows a restriction enzyme map of vaccinia virus vector pBSF2-16.

The present invention will now be more specifically illustrated as hereunder.

In the present specification, the term MBP not only means that of a natural type but also covers any protein in which the amino acid sequence of the natural type is modified by, for example, means of substitution, deletion, addition or insertion of the amino acid residues so far as such a protein still exhibits the activity as MBP. Examples of the MBP of a natural type mentioned here are those derived from human being and rabbit although the present invention is not limited thereto but covers those derived from other organisms such as animals and plants and also those derived from microorganisms such as bacteria, yeasts, *Actinomycetes*, filamentous fungi, *Ascomycetes* and *Basidiomycetes*.

In the present specification, there is no particular limitation for the gene which codes for MBP so far as the gene codes for the MBP and the protein having the MBP activity as mentioned above. Thus, the gene which codes for the protein having an MBP activity is covered by the present invention even if the said gene is subjected to a modifying treatment used in genetic engineering such as substitution, deletion, addition and insertion.

In the present invention, the object can be achieved by introducing the MBP into cancer cells and the surrounding tissues thereof or into tissues of a non-diseased part. In introducing the MBP, it may be directly introduced into cancer cells by means of a direct administration to cancer cells such as a microinjection method where the activity of MBP is maintained or by means of a subcutaneously administering method or a intravenously administering method where the activity of MBP is maintained. Moreover, an object of the present invention can be achieved by, for example, introduction of the gene which codes for MBP using virus or the like or by introduction of the gene coding for MBP by means of a subcutaneously administering method or the like whereby MBP is expressed.

Thus, when the pharmaceutical agent of the present invention is used, it is now possible to introduce the MBP or the gene coding for MBP into cancer cells and the surrounding tissues thereof or into tissue of a non-diseased part whereby the growth of cancer can be suppressed.

MBP or gene which codes for MBP may be directly injected into the diseased part on the tissue surface or the surrounding tissues thereof. It is also possible to directly inject into the diseased part inside of the tissues or the surrounding tissues thereof and a drug delivery system (DDS) may be applied as well. Any DDS may be applied so far as it is a system which is specific to cancer cells and, for example, it may be selected from common systems utilizing cancer cell receptors, cancer-specific antibody, etc. It is also possible that ligand or receptor which is specific to organs or cells around the surrounding tissues is utilized whereby the MBP is specifically introduced into those organs. Incidentally, it is a very effective method for suppressing the growth of microcancer to excise the cancer tissues by means of a surgical operation followed by applying the pharmaceutical agent of the present invention to the non-cancerous parts.

When a pharmaceutical agent in which the MBP of the present invention or gene coding for the said MBP is an effective component is used to cancer cells and the surrounding tissue thereof or to tissues of a non-diseased part, it goes without saying that the said pharmaceutical agent is to be used in such a manner that the agent works most effectively. The anticancer agent of the present invention is to contain the MBP or the gene coding for the MBP to a pharmaceutically acceptable extent and can be made into pharmaceutical preparations by the same manner as in common genetic remedies or protein-containing agents. The preparations may contain vehicles, fillers, stabilizers, thickeners, etc. therein.

Dose of the MBP or the gene coding for the said MBP which is used as an anticancer agent of the present invention may be appropriately decided and adjusted by taking its dosage form, method of use and age, body weight, degree of progress of disease, etc. of the patient into consideration. For example, in the case of protein, the dose for adults is 0.01.g-1 g/kg for each administration. When recombinant virus for expression of protein is used, the dose for adults is $1\times10^2 \sim 1\times 10^{12}$ PFU (plaque forming unit) for each administration. Needless to say, the dose may vary depending upon various conditions and, therefore, the less dose than above may be sufficient in some cases or the more dose than the above may be necessary in other cases.

MBP or gene coding for the MBP contained in the anticancer agent of the present invention is a substance found in vivo and has no toxicity.

With regard to the MBP used in the present invention, its detailed protein chemical properties have been clarified already and, for example, it can be prepared from human serum by the steps as shown in the following Table 1 according to a method by Kawasaki, et al. [*Journal of Biochemistry*, 94(3), 937-947 (1983)].

TABLE 1

| Steps | Specific Activity [Unit/Protein (.g)] | Yield (%) |
|---|---|---|
| 1. Serum | 0.009 | 100 |
| 2. Sepharose 4B-mannan 1 | 19.7 | 4.5 |
| 3. Sepharose 4B-mannan 2 | 70.9 | 51.5 |
| 4. Sepharose 4B-mannan 3 | 79.5 | 43.6 |
| 5. Sepharose CL-6B | 160.6 | 29.6 |

Binding activity of MBP can be measured using a $^{125}$I-labelled mannan ($^{125}$I-mannan) according to a method mentioned in *Journal of Biochemistry*, 94(3), 937-947 (1983). Specific activity of MBP is expressed in terms of the bound $^{125}$I-mannan (ng)/weight of protein (.g). Amount of the protein is measured by a Lowry's method using bovine serum albumin as a standard.

Gene which codes for MBP may, for example, be obtained from a human liver cDNA library according to a method of Kurata, et al. [*Journal of Biochemistry*, 115(6), 1148-1154 (1994)].

The amino acid sequence of the mature protein of human MBP obtained by the method is shown in SEQ ID NO:1 of the appended Sequence Listing and the nucleotide sequence for the gene coding therefore is shown in SEQ ID NO:2 of the Sequence Listing.

When such a gene or a part thereof is used as a probe, it is possible to prepare a gene which hybridizes to the said gene and codes for protein having an MBP activity. In addition, when a primer is designed from the said gene or a part thereof and then a PCR is carried out using the said primer, it is possible to prepare a gene which codes for protein having an MBP activity.

An example for the hybridization is that a Nylon membrane where a genome DNA obtained from organism, microorganism, etc. or a cDNA library is immobilized is prepared and is blocked at 65 in a prehybridization solution containing 0.5% of SDS, 5×Denhardt's solution [containing 0.1% of bovine serum albumin (BSA), 0.1% of polyvinylpyrrolidone and 0.1% of Ficoll 400], 100 g of salmon sperm and 6×SSC (1×SSC contained 0.15M of NaCl and 0.015M of sodium citrate; pH 7.0). After that, each probe labeled with $^{32}$P is added followed by incubation at 65 for four hours to overnight. The Nylon membrane is washed with 6×SSC for ten minutes at room temperature and with 0.1% SDS for 30 minutes at 45 and the DNA hybridizing with the probe can be detected by an autoradiography. Incidentally, genes having various homologies are able to be prepared by using various conditions such as washing.

It is also possible that, when a modifying treatment by means of genetic engineering such as substitution, deletion, addition and insertion is carried out to the gene represented by SEQ ID NO:2 of the Sequence Listing, the gene which hybridizes to the gene represented by SEQ ID NO:2 of the Sequence Listing and codes for the protein having an MBP activity is prepared.

Examples of the applicable method for carrying out the modification are a method utilizing an amber modification [gapped duplex method; cf. *Nucleic Acids Research*, 12(24), 9441-9456 (1984)], a method utilizing a restriction enzyme site [*Analytical Biochemistry*, 200, 81-88 (1992); and *Gene*, 102, 67-70 (1991)], a method utilizing dut (dUTPase) and ung (uracil DNA glucosylase) modification [Kunkel's method; cf. *Proceedings of the National Academy of Sciences of the U.S.A.*, 82, 488-492 (1985)], a method utilizing an amber modification using DNA polymerase and DNA ligase [an oligonucleotide-directed Dual Amber (ODA) method; cf. *Gene*, 152, 271-275 (1995)] and a method by a PCR using two kinds of primers for introduction of modification to which recognition site of restriction enzyme is added (U.S. Pat. No. 5,512,463).

It is also possible to use commercially available kits such as Mutan®-G (manufactured by Takara Shuzo) using a gapped duplex method, Mutan®-K (manufactured by Takara Shuzo) using a Kunkel's method, Mutan®-Express Km (manufactured by Takara Shuzo) using an ODA method, QuikChange™ Site-directed Mutagenesis Kit (manufactured by Stratagene) using a primer for introduction of modification and *Pyrococcus furiosus*, TaKaRa LA-PCR in vitro Mutagenesis Kit (manufactured by Takara Shuzo) utilizing a PCR, and Mutan®-Super Express Km (manufactured by Takara Shuzo).

It is possible to confirm by measuring the MBP activity according to a method described in *Journal of Biochemistry*, 94(3), 937-947 (1983) or *Journal of Biochemistry*, 115(6), 1148-1154 (1994) whether the gene prepared as such is a gene which codes for the protein having an MBP activity.

Those genes and expressed protein obtained by the said genes can be used as a pharmaceutical agent of the present invention as well.

When the pharmaceutical agent of the present invention is introduced into cancer cells using the gene per se coding for MBP, introduction of the gene coding for MBP can be easily carried out if, for example, the gene coding for MBP and the recombinant vector having a regulatory gene related thereto are used. With regard to the regulatory gene, it is possible, in addition to a vector having a promoter for the gene per se coding for MBP, to use those having other effective promoters such as vaccinia virus A inclusion (ATI) promoter, SV 40 promoter, LTR promoter derived from retrovirus, heat shock promoter, metallothionein promoter and actin promoter.

Those vectors are able to be introduced into cancer or into the cells which are not yet tumorigenically transformed in a form of a vector remaining outside of the chromosomes in the cells. Under such a state, it is possible that the gene is expressed by cells from the position outside of the chromosome, produces the MBP and increases the MBP concentration within the cell whereupon an object of the present invention can be achieved.

Vector for extrachromosomal retention has been known in the art and an appropriate vector may be used. With regard to a method for introducing the said vector into cells, an electroporation method, a coprecipitation method with calcium phosphate, a virus transduction method, etc. have been known in the art and it is within a range of daily work that what method is to be selected.

It is further possible that the gene encoding MBP is introduced into cancer or into cells which are not yet tumorigenically transformed in a form of a vector to be integrated into chromosome. Under such a state, it is possible that gene is retained in chromosome, expressed by cells, produces the MBP and increases the MBP concentration within the cell whereupon an object of the present invention can be achieved.

In introducing the MBP gene into cells, the vector containing the said gene can be efficiently introduced by the use of virus vector. With regard to such a vector, it is possible to use that which has been known to transport the desired DNA to cells and has a high infecting efficiency such as vaccinia virus vector, retrovirus vector, adenovirus vector, adeno-associated virus vector or non-proliferating recombinant virus vector. Particularly in the case of non-proliferating recombinant vector, the recombinant virus does not grow after introduction into the desired cells and, therefore, it is to be used freshly every two weeks to every two months but there is an advantage that administering amount can be adjusted at each of such occasions. It is also possible to use an artificially prepared spherical capsular liposome which is a non-viral vector such as membrane-attached liposome and cationic liposome.

An example of a method for the construction of recombinant virus which is desirable as a pharmaceutical agent of the present invention will be mentioned as follows. Thus, cDNA of human MBP is introduced into SmaI and SacI sites of vaccinia virus vector pBSF2-16 (FIG. 1) constructed by a method mentioned in *Archives of Virology*, 138, 315-330 (1994) to prepare a recombinant vector pBSF2-16/MBP (FIG. 2) of MBP being controlled by ATI hybrid promoter (a promoter in which ATI promoter is combined with several 7.5 kDa promoters arranged in series). The recombinant vector pBSF2-16/MBP and vaccinia virus DNA of a wild type are co-transfected to COS-7 cells and the recombinant vaccinia virus is selected by, for example, means of expressing amount of MBP or a hemagglutinin phenotype whereupon MBP expression recombinant vaccinia virus can be obtained.

With regard to an anticancer effect, an effect for suppressing the growth of cancer can be evaluated, for example, by such a manner that human cancer cells are inoculated to a nude mouse, the pharmaceutical agent of the present invention is then administered thereto and the growing ability of the cancer tissues thereafter is measured. Thus, human colon cancer cell strain SW1116 is subcutaneously inoculated to a KSN nude mouse and, three weeks thereafter, the above MBP expressing recombinant vaccinia virus is administered into tumor or subcutaneously administered to non-diseased part. After two weeks, the MBP expressing recombinant vaccinia virus is administered again in the same manner and the size of the tumor after the administration is measured whereby the suppressing ability to the growth of cancer cells can be evaluated.

EXAMPLES

The present invention will now be more specifically illustrated by way of the following examples although the present invention is not limited to those examples.

Example 1

Construction of Expression Vector and Recombinant Vaccinia Virus.

cDNA clone H-3-1 containing the full length of coding region of human MBP [*Journal of Biochemistry*, 115(6), 1148-1154 (1994)] was subcloned to SmaI and SacI sites which were immediately downstream to ATI hybrid promoter (a promoter in which ATI promoter and several 7.5 kDa promoters are arranged in series are combined) of vaccinia virus vector pBSF2-16 [*Archives of Virology*, 138, 315-330 (1994)] to prepare an MBP expression plasmid pBSF2-16/MBP controlled by ATI hybrid promoter.

Figure 2:
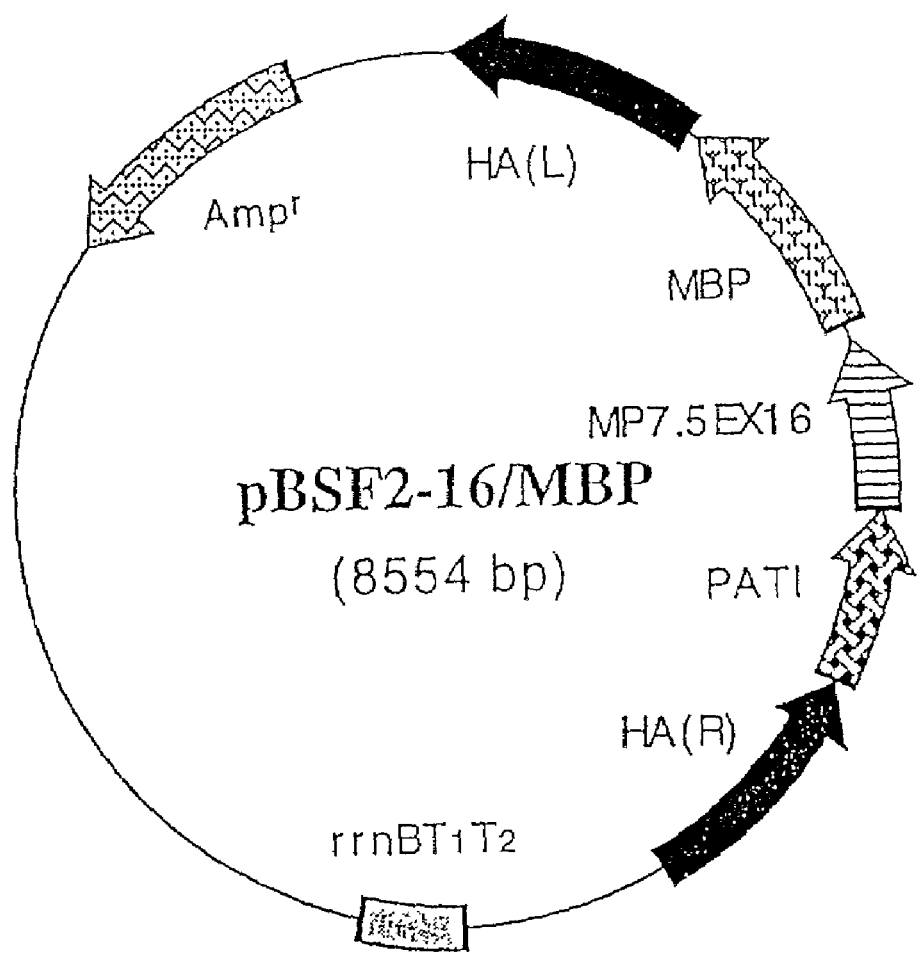
FIG. 2 is a drawing which shows a type chart of MBP expression plasmid pBSF2-16/MBP.

FIG. 1 shows a restriction enzyme map of the vaccinia virus vector pBSF2-16 while FIG. 2 shows a typical chart of the MBP expression plasmid pBSF2-16/MBP.

After that, an IBT(=isatin—thiosemicarbazone)-dependent vaccinia virus strain [*Virology*, 155, 97-105 (1986)] was infected to COS-7 cells (ATCC CRL 1651). Then pBSF2-16/MBP and genome DNA extracted from virion of a wild type vaccinia virus WR strain were introduced, using a DOTA reagent (manufactured by Boehringer Mannheim), into the COS-7 cells infected with the IBT-dependent vaccinia virus strain whereupon an MBP recombinant vaccinia virus was prepared.

Incidentally, the recombinant vaccinia virus was selected according to a hemagglutinin phenotype by a method mentioned in *Archives of Virology*, 138, 315-330 (1994) and detected in RK-13 cells (ATCC CCL 37) by means of an ELISA. Titer of the virus was measured by a plaque formation method and was expressed as a plaque forming unit (PFU).

Example 2

Evaluation of Anticancer Effect.

Evaluation of the anticancer effect in vivo was carried out as follows.

Thus, human colon cancer cells SW 1116 strain (ATCC CCL 233) was subcutaneously inoculated in an amount of $10^7$ cells per mouse (KSN nude mouse; manufactured by Japan SLC) and, three weeks thereafter, the MBP recombinant vaccinia virus mentioned in Example 1 was administered into tumor of the diseased part or was administered subcutaneously to non-diseased part in an amount of $5\times10^6$ PFU per mouse. As a control, the same amount of vaccinia virus WR strain of a wild type was administered into tumor of the diseased part.

Figure 3:
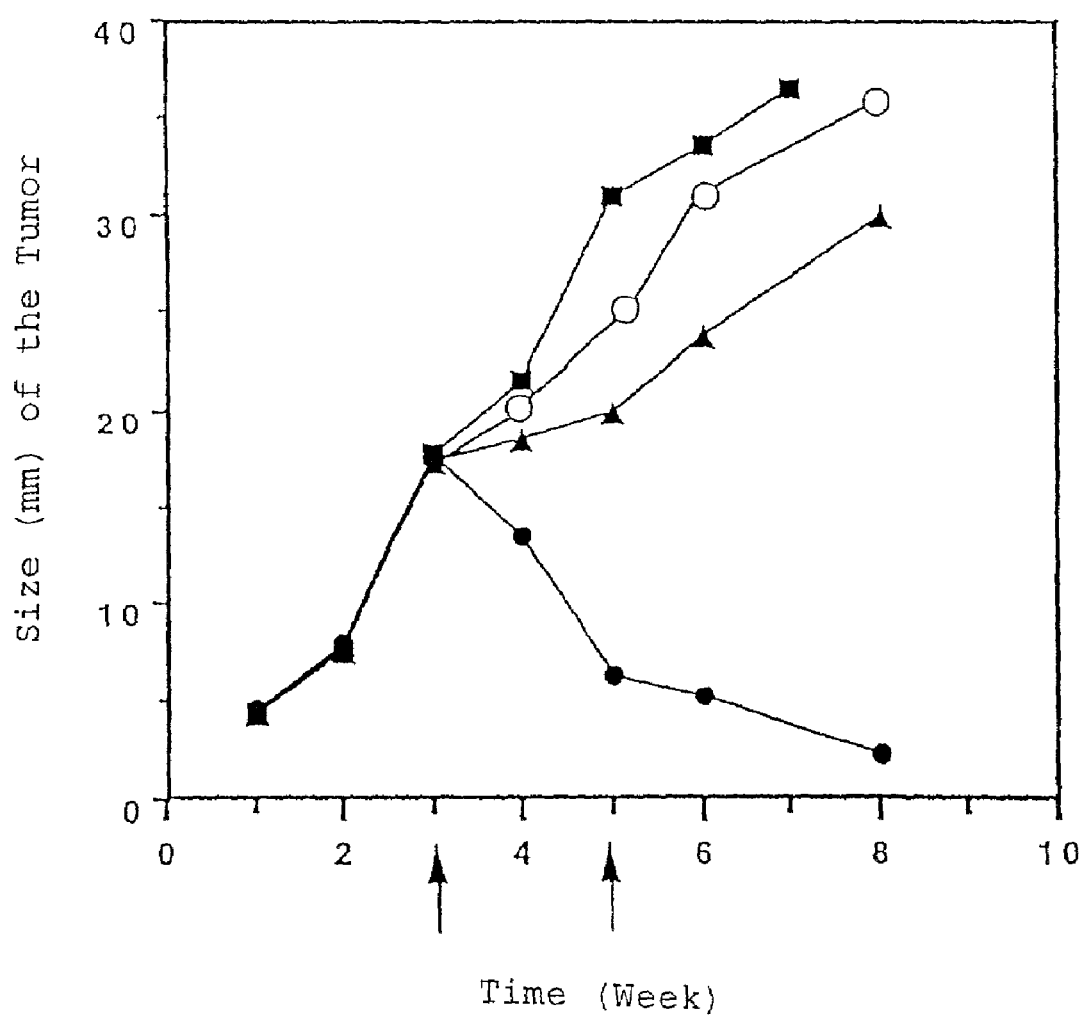
FIG. 3 is a drawing which shows the result of the experiments for evaluating the anticancer effect in vivo.

After two weeks, the MBP recombinant vaccinia virus or the vaccinia virus WR strain of a wild type was administered in the same amount and in the same manner and the size of the tumor after the administration was measured whereby the suppressing ability to the growth of cancer cell was evaluated. As a control, a group where a physiological saline solution was subcutaneously administered to the non-diseased part was used. The result is shown in FIG. 3. Thus, FIG. 3 is a drawing which shows the result of the experiments for evaluating the anticancer effect in vivo where an ordinate indicates the size (mm) of the tumor while an abscissa indicates week numbers after transplantation of the cancer cells. In the drawing, black squares indicate a group where a physiological saline solution was subcutaneously administered to the non-diseased part, open circles indicate a group where vaccinia virus WR strain of a wild type was administered into tumors of the diseased part, closed circles indicate a group where an MBP recombinant vaccinia virus was administered into tumors of the diseased part and black triangles indicate a group where an MBP recombinant vaccinia virus was subcutaneously administered to the non-diseased part. The arrows in the drawing indicate the weeks when the MBP vaccinia virus, vaccinia virus WR strain of a wild type and physiological saline were administered.

It is apparent from FIG. 3 that, when the MBP recombinant vaccinia virus of the present invention is administered into tumors of the diseased part, the tumors clearly became smaller and that, even when it was subcutaneously administered to the non-diseased part, a significant suppression of growth of cancer cells was observed as compared with the controls where vaccinia virus WR strain of a wild type and physiological saline solution were administered.

Merit of the Invention

In accordance with the present invention, an anticancer agent which enhances the MBP concentrations in cancer cells and the surrounding tissues thereof or in the tissues of non-diseased part or, in other words, the agent containing an MBP or gene thereof as an effective component is offered. The said anticancer agent is useful in the field of therapy of cancer.

What is claimed is:

1. A method of treating human cancer comprising administering a gene encoding a mannan-binding protein comprising SEQ ID NO:1, wherein administering said gene includes injecting said gene directly into a tumor of the diseased part, wherein said gene is integrated in a virus vector.

2. The method of claim 1, wherein the gene comprises SEQ ID NO:2.

3. The method of claim 1, wherein the virus vector is a vaccinia virus vector.

* * * * *